United States Patent [19]
Engeron

[11] Patent Number: 6,102,701
[45] Date of Patent: Aug. 15, 2000

[54] RETRACTOR APPARATUS

[76] Inventor: Michael G. Engeron, 206 Mystic Blvd., Houma, La. 70360-2762

[21] Appl. No.: 09/234,588

[22] Filed: Jan. 21, 1999

[51] Int. Cl.[7] .................................................. A61C 5/00
[52] U.S. Cl. ......................................................... 433/140
[58] Field of Search ........................... 433/140; 600/237, 600/238, 239, 240

[56] References Cited

U.S. PATENT DOCUMENTS

| | | |
|---|---|---|
| 548,817 | 10/1895 | Platt . |
| 730,184 | 6/1903 | Witter . |
| 744,204 | 11/1903 | Jordan . |
| 903,344 | 11/1908 | Wackler . |
| 1,474,497 | 11/1923 | Stolper ................................ 433/140 X |
| 2,125,980 | 8/1938 | Basil . |
| 2,831,480 | 4/1958 | Milano ..................................... 128/15 |
| 4,259,068 | 3/1981 | Stephens ................................. 433/140 |
| 5,466,153 | 11/1995 | Poindexter .............................. 433/140 |
| 5,730,597 | 3/1998 | Luttrell ................................... 433/140 |

*Primary Examiner*—Nicholas D. Lucchesi
*Attorney, Agent, or Firm*—Garvey, Smith, Nehrbass & Doody, LLC

[57] ABSTRACT

An improved retractor apparatus for conducting orthodontic procedures in a dry field, the retractor including a first arm portion for extending along the outer surface of a patient's cheek that can be grasped by the orthodontist performing the procedure; a second lower lip depressor portion concavely formed for pressing against the lower lip as the orthodontist grasps the handle portion, a third cheek retractor portion extending from the bridge (lip retractor) portion into the mouth of the patient and formed in a biconvex fashion to curve along the inner surface of the cheek of the patient; an upper lip retractor portion that retracts and elevates the upper lip as the apparatus is manipulated by the dentist, a bridge member situated at the confluence of the first arm, (handle) portion, the second arm (lower lip depressor) portion, the third arm (cheek retractor) portion and the fourth arm (upper lip retractor) portion. The long axis of the handle portion extends at an incline relative to the lip depressor and cheek retractor portions for defining a thin waist portion on the handle so that the end of the handle may be grasped to depress the patient's lower lip, retract the upper lip, and to extend the cheek of the patient outward so as to provide an increased volume of space for conducting the orthodontic procedure in a dry field.

14 Claims, 7 Drawing Sheets

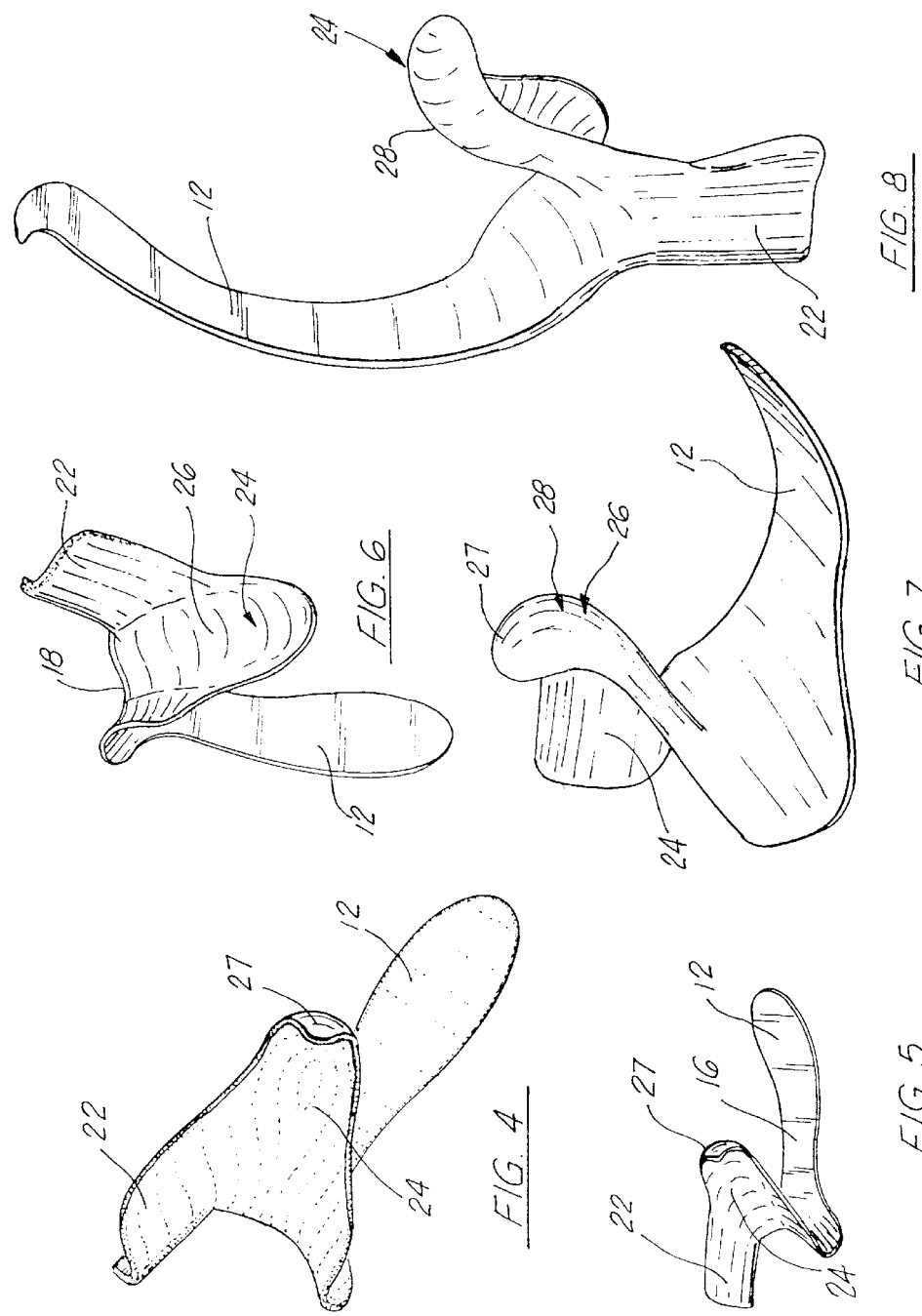

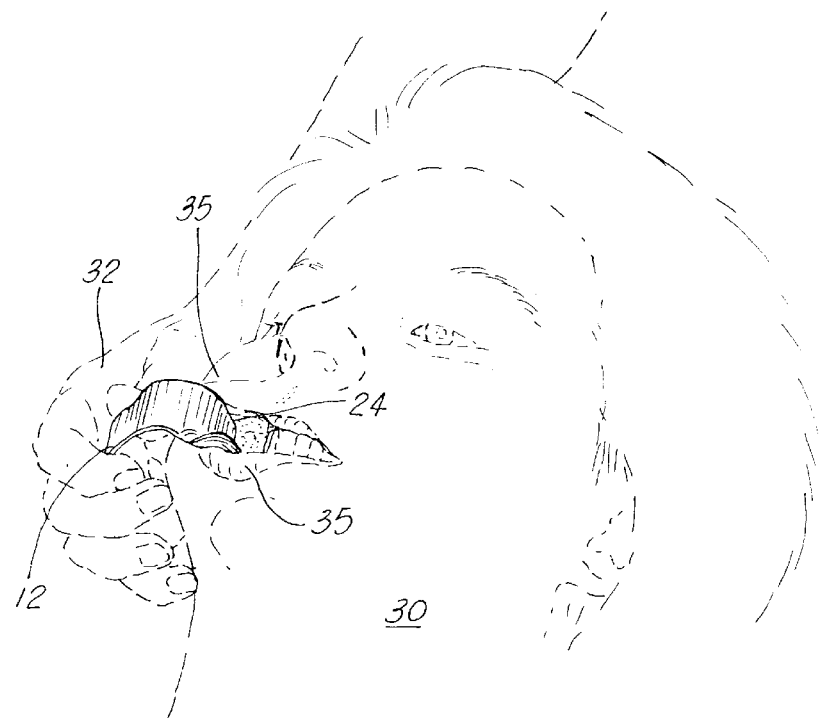
FIG. 10
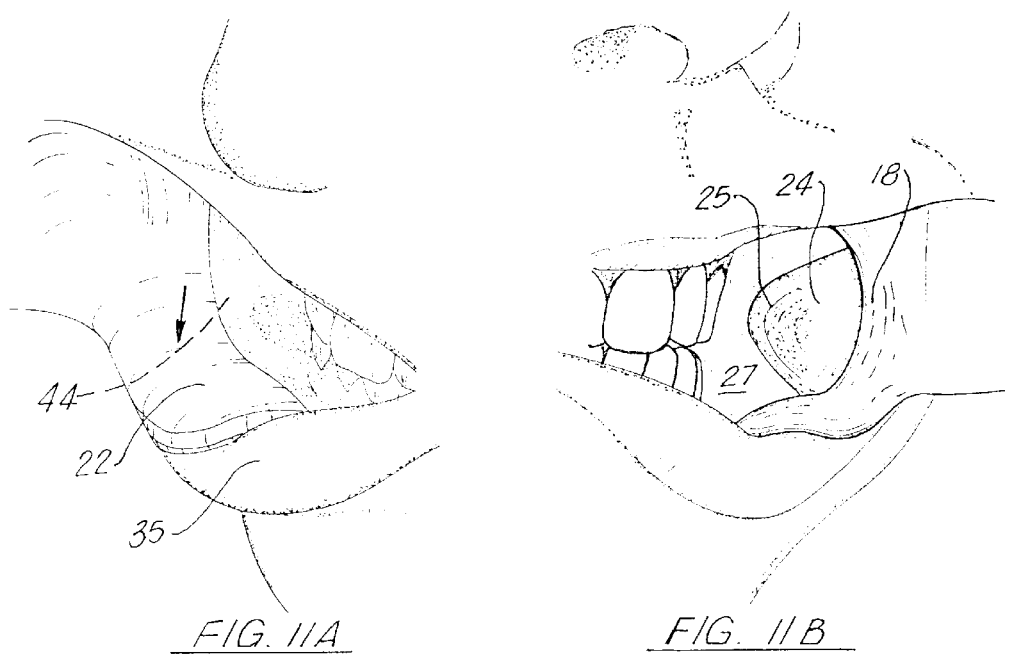
FIG. 11A
FIG. 11B

RETRACTOR APPARATUS

CROSS-REFERENCE TO RELATED APPLICATIONS

Not applicable

STATEMENT REGARDING FEDERALLY SPONSORED RESEARCH OR DEVELOPMENT

Not applicable

REFERENCE TO "MICROFICHE APPENDIX"

Not applicable

BACKGROUND OF THE INVENTION

1. Field of the Invention

The apparatus of the present invention relates to dental appliances. More particularly, the present invention relates to an improved retractor apparatus for retracting certain areas of a patient's mouth such as the lips and the cheek in order to allow greater access to the patient's mouth during dental work such as orthodontics.

2. General Background

Quite often in conducting dental work on a patient, such as orthodontics or the like type of operation, there is a requirement that the patient's lip and cheek be positioned so as to allow the dentist maximum access to the area of the mouth in which the operation will be conducted, which in most cases is in the area of the rear teeth such as the wisdom teeth or molars. Furthermore, during certain procedures such as those conducted by an orthodontist, it is important to retract the soft tissue away from the teeth undergoing the orthodontic procedure in order to provide comfortable access to a dry field, including the buccal surfaces of maxillary and mandibular second molars simultaneously, for allowing bonding of orthodontic appliances, such as braces, to the teeth.

While this is an important aspect of an appliance that would be utilized in order to meet these requirements, it is also important that the patient who is normally awake and aware and unanesthetized, be in as much comfort as possible during the procedure.

For example, there are appliances known in the art which have been utilized for affording access into a patient's mouth during a procedure. One of the more common types of retractors is called a Bishop Retractor, which is a surgical instrument apparatus which is grasped by a standing surgeon or an assistant who holds the cheek of the patient out with one hand while he, the surgeon, conducts a surgical procedure with the other hand. The Bishop retractor is a rather simple instrument, and is used primarily, if not exclusively, in surgical procedures while the patient is anesthetized.

Secondly, U.S. Pat. No. 5,730,597, which was patented by Clifford Luttrell, and assigned to the United States of America, teaches a flat, buccal retractor which attempts to solve the problem in the art. However, this instrument butt or end is quite narrow and sharp which would lead to discomfort for the patient, and also would not allow for keeping soft tissue and saliva out of the field in an orthodontic procedure The narrow sharp-ended cheek retractor of Luttrell is designed to be used in an operating room setting by a standing surgeon on a fully anesthetized patient. It is designed to retract unsurgerized tissue to allow access to that soft tissue on the stretch to facilitate surgerizing the stretched tissue. Furthermore, it could be used to retract surgerized tissue to allow visualization of, and access to, the bony maxilla beneath the soft tissue in order to allow instrumentation, irrigation, and cutting of the bony jaw with a rotary or reciprocating instrument. Again, these procedures are normally done in a wet field on an anesthetized patient by a standing surgeon.

The Luttrell instrument, in one embodiment, retracts either the left upper lip or the right lower lip, but not simultaneously. The other, mirror form of the instrument retracts the left lower lip or right upper lip, but again, not simultaneously. Therefore, there is a need in the industry for providing an improved retractor apparatus which would allow a dentist to work in a dry field for doing, in particular, orthodontic procedures, and shaped in order to have greater comfort for the patient, and so constructed so that the instrument allows the left upper and lower lips, as well as the lip commissure and cheek, to be retracted simultaneously by the orthodontist. The mirror image instrument would be used to retract the right upper and lower lips, as well as the right commissure and cheek. Furthermore, there is a need to allow such a device to be utilized wherein the dentist or orthodontist may conduct the procedure while being seated rather than having to hover over the patient, which one may have to do if one utilized the Luttrell device in the procedure.

BRIEF SUMMARY OF THE INVENTION

The apparatus of the present invention solves the shortcomings in the art in a simple and straightforward manner. What is provided is an improved retractor apparatus for conducting orthodontic procedures in a dry field, the retractor including a first arm portion for extending along the outer surface of a patient's cheek that can be grasped by the orthodontist performing the procedure; a second lower lip depressor portion concavely formed for pressing against the lower lip as the orthodontist grasps the handle portion, a third cheek retractor portion extending from the bridge (lip retractor) portion into the mouth of the patient and formed in a biconvex fashion to curve along the inner surface of the cheek of the patient; a fourth upper lip retractor portion that retracts and elevates the upper lip as the apparatus is manipulated by the dentist, a bridge member situated at the confluence of the first arm, (handle) portion, the second arm (lower lip depressor) portion, the third arm (cheek retractor) portion and the fourth arm (upper lip retractor) portion. The long axis of the handle portion extends at an incline relative to the lip depressor and cheek retractor portions for defining a thin waist portion on the handle so that the end of the handle may be grasped to depress the patient's lower lip, retract the upper lip, and to extend the cheek of the patient outward so as to provide an increased volume of space for conducting the orthodontic procedure in a dry field.

Therefore, it is a principal object of the present invention to provide a dental appliance which allows an orthodontist to conduct procedures on a patient who is awake while in greater comfort and retracting the lips and cheek portions away from the patient's teeth in order to establish a dry field comfortably within the mouth;

It is a further principal object of the present invention to provide an improved retractor apparatus for placement in a patient's mouth so that the apparatus may be held by a handle portion while the orthodontist is sitting, and as the handle portion is pulled on a slight incline, there is provided a lower lip depressor portion, an upper lip retractor portion, and cheek retractor portion for establishing greater access to the patient's dry teeth while the patient is awake and substantially comfortable;

It is a further object of the present invention to provide an improved retractor apparatus which provides for substantially greater operational features in the prior art, and allows an orthodontist to undertake procedures while being seated yet while simultaneously having access to the patient's mouth in a dry field.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIGS. 1–8 illustrate various views of the preferred embodiment of the improved retractor apparatus of the present invention;

FIG. 10 illustrates a view of the apparatus in a patient's mouth while the apparatus is held by the orthodontist;

FIGS. 11A and 11B illustrate the lower lip depressor portion, the bridge portion, the upper lip retractor portion and the cheek retractor portion respectively of the apparatus of the present invention;

DETAILED DESCRIPTION OF THE INVENTION

Figure 1:
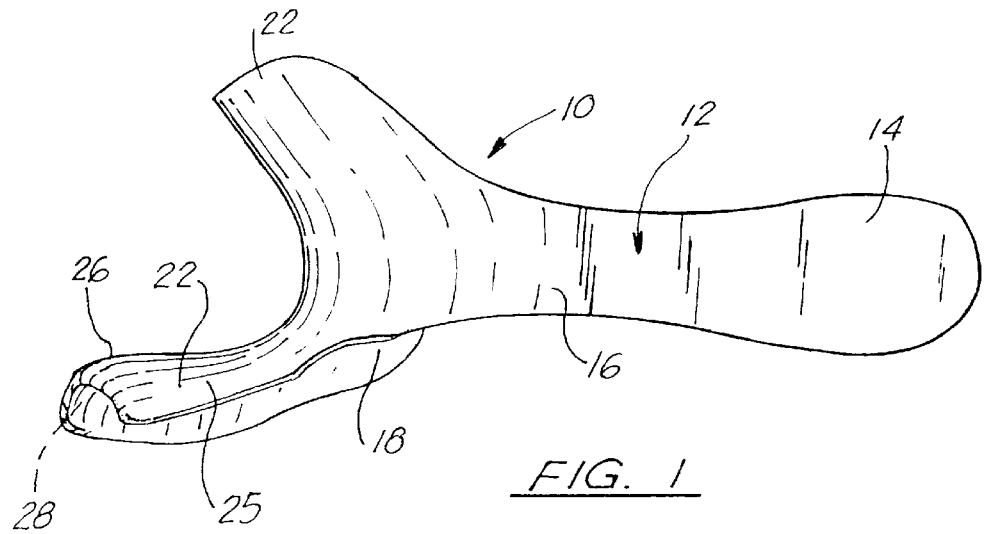

FIGS. 1–14 illustrated the preferred embodiment of the apparatus of the present invention by the numeral 10. As illustrated in various views of the apparatus, particularly as seen in FIGS. 1–8, there is illustrated improved retractor apparatus 10 which would comprise various portions, some portions which are more clearly illustrated in certain figures than others. For example, in FIG. 1 there is illustrated apparatus 10 having the exterior handle portion 12, handle portion 12 having an enlarged end portion 14 and a center waist portion 16 which then would emerge into a substantially centralized bridge portion 18. The handle portion 12 is shaped so that the thin waist portion 16 allows for firmly grasping the handle during use and retraction without allowing the fingers to slip from the handle 12.

Figure 2:
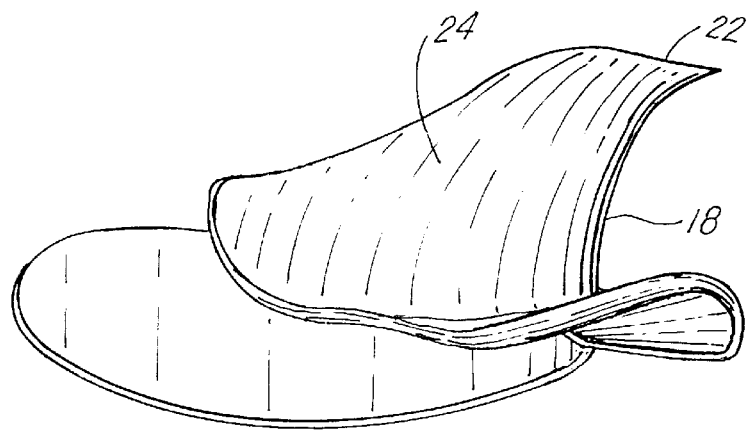
Figure 3:
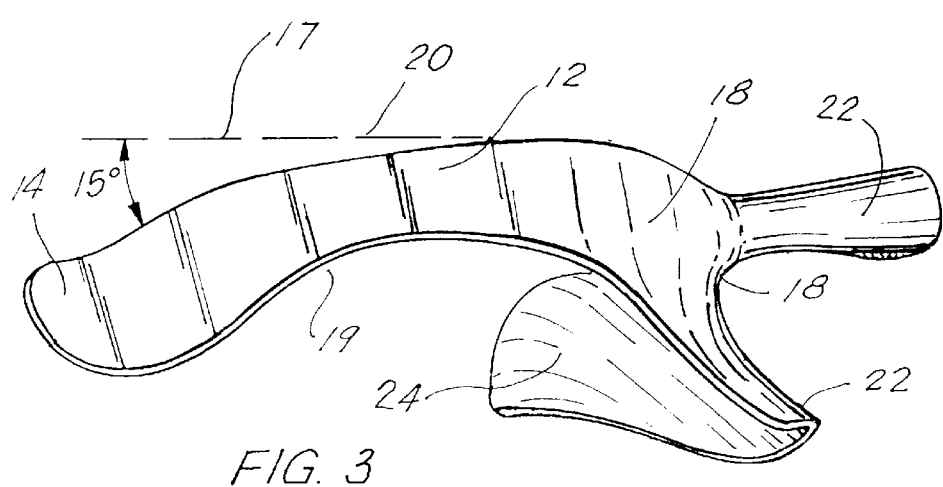

For purposes of further explanation of the construction of handle portion 12, reference is made to FIG. 3 where handle portion 12 is illustrated, and it is seen that the handle portion 12 is substantially elongated and terminates in the enlarged portion 14, the handle portion being somewhat thin in overall thickness along edge 19, and having an overall arcuate shape along line 20 as seen in FIG. 3. Again, it is seen as the handle portion terminates at bridge portion 18 there is formed the three other principal portions of the apparatus 10. There is first seen the lower lip depressor portion 22 and as seen clearly in FIG. 1, the cheek retractor portion 24 as seen more clearly in FIG. 2, and the upper lip retractor portion 29 as seen in FIGS. 1, 2 and 3. As seen in FIGS. 1–8, the lower lip depressor portion 22 includes an arcuate extended member 25 having an outer convex surface 26 and an interior concave surface 28. The concavity 28 is formed the length of the lip depressor portion 22 and would essentially engage the lower lip during use of the apparatus as will be explained further. The upper lip retractor portion 29 is also concave along surface 31 to engage and retract the upper lip comfortably. The bridge portion serves to retract the commissure of the mouth and as the confluence of the handle, upper lip retractor, lower lip retractor, and cheek retractor portions.

Turning now to the cheek retractor portion 24, it is seen that the cheek retractor portion 24 is seen clearly for example in FIG. 6. Again, as seen in FIG. 6 there is illustrated the handle portion 12, the lower lip depressor portion 22, the cheek retractor portion 24 and the upper lip retractor portion 29. As illustrated, cheek retractor portion 24 is formed from the bridge portion 18 of the apparatus 10, and forms substantially a U shape extending substantially in the same direction of handle 12. The cheek retractor portion 24 has a concave surface 26 and a substantially convex surface 28 as seen in FIGS. 6–8, the convex surface 28 being inserted into the mouth of the patient and pressing against the interior surface of the cheek as it is placed within the mouth of the patient. Further, which is not clearly seen in FIG. 6, but is seen in FIG. 7, is that the cheek retractor portion 24, which illustrates the concave surface 28, would be pressed against the patient's cheek 39 as will be described further. However, as seen more clearly in FIG. 7, concave surface 28 terminates in a biconvex end portion 27 which would when placed in the patient's mouth press against the rear wall of the patient's mouth deep in the vestibule 44 while the apparatus is being used. Again, this biconvex portion 27 would be seen again in FIG. 9B as will be described further.

Figure 9A:
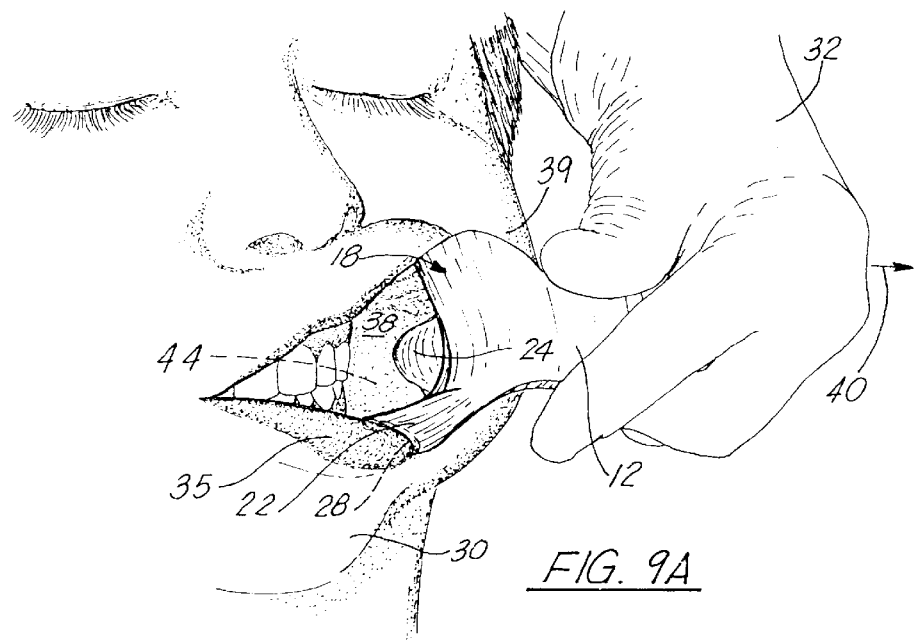
FIGS. 9A and 9B illustrate views of the apparatus placed in a patient's mouth during an orthodontic procedure.
Figure 9B:
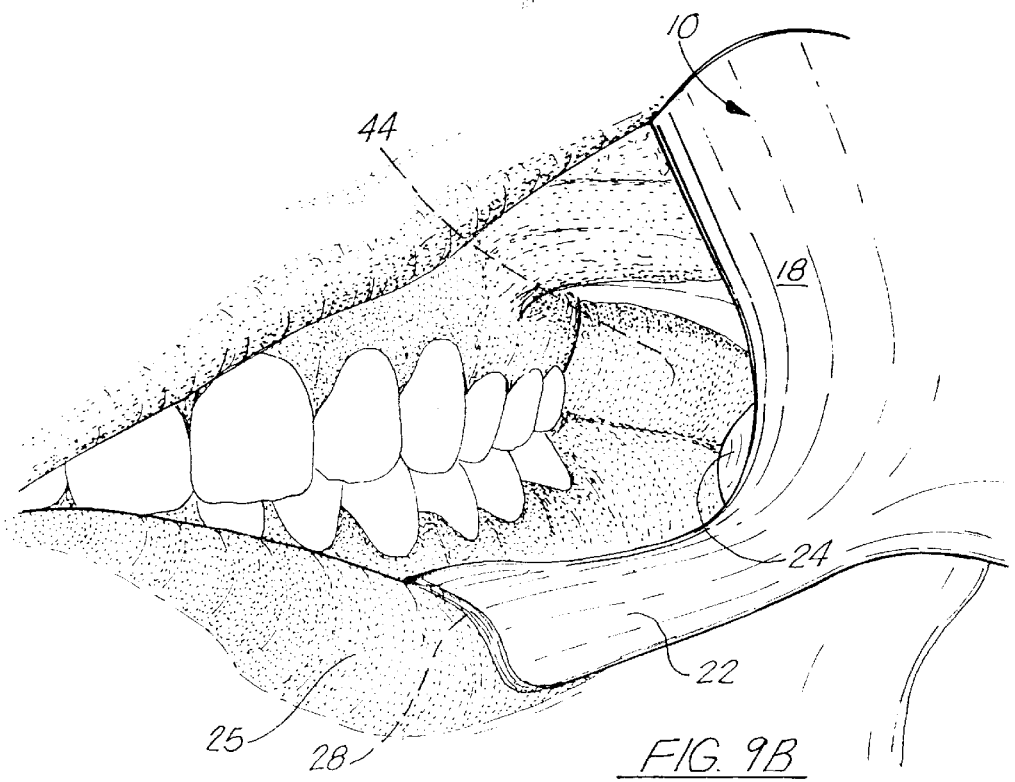

For example, turning now to FIG. 9A, there is illustrated a patient 30 having the apparatus 10 inserted in the patient's mouth. As clearly seen, the hand 32 of the dentist is holding the handle portion 12 of the apparatus while the lower lip depressor portion 22 is holding the lower lip 35 of the patient 30 in the channel 28 formed by the lip depressor portion 22. Simultaneously, the cheek retractor portion 24 has been inserted and is pressing against the interior surface 38 of the patient's cheek, and retracting the cheek 39 of the patient outward in the direction of arrow 40. In this manner, there is then seen the lower lip 35 being depressed by depressor portion 22 cheek 39 being extended outward by the cheek retractor portion 24, and the upper lip being retracted upward by portion 29. There is defined a dry vestibule 44 within the mouth of the patient 30 for conducting orthodontic procedures. This is seen again in close up view in FIG. 9B as was described earlier.

Figure 12A:
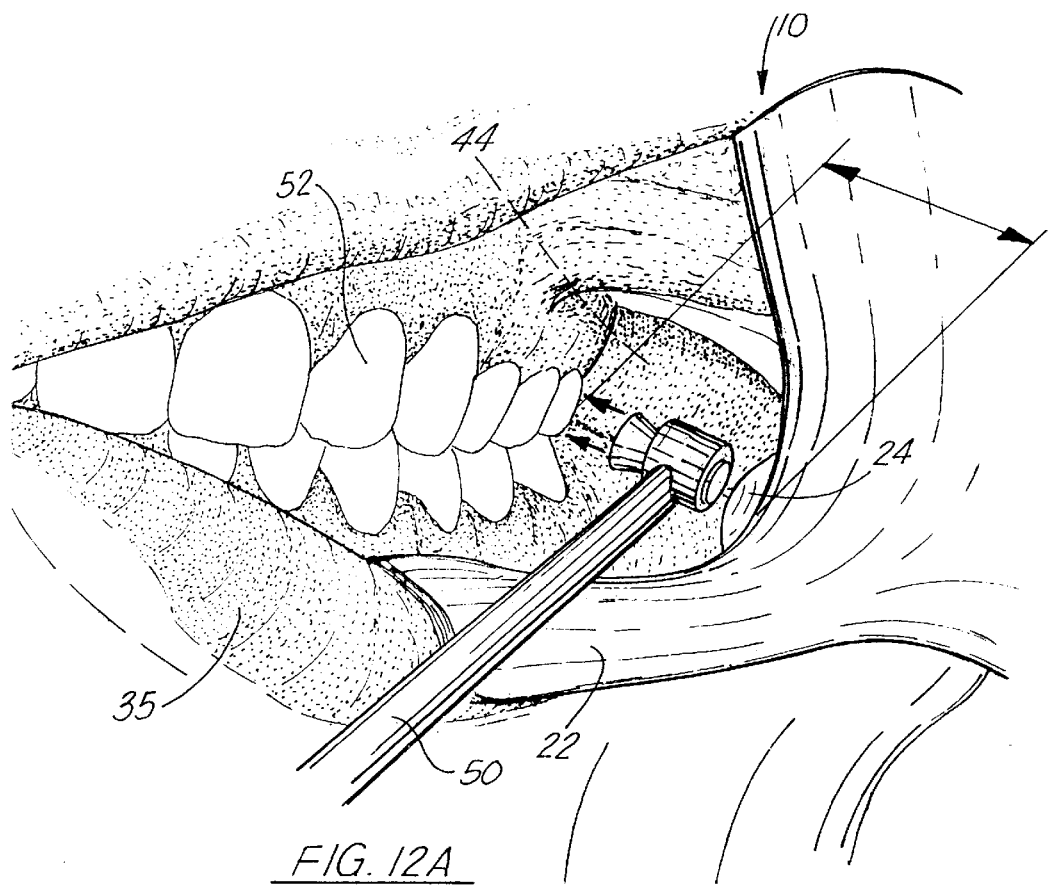
FIGS. 12A and 12B illustrates the apparatus of the present invention being utilized with a dental appliance such as a polishing instrument.
Figure 13:
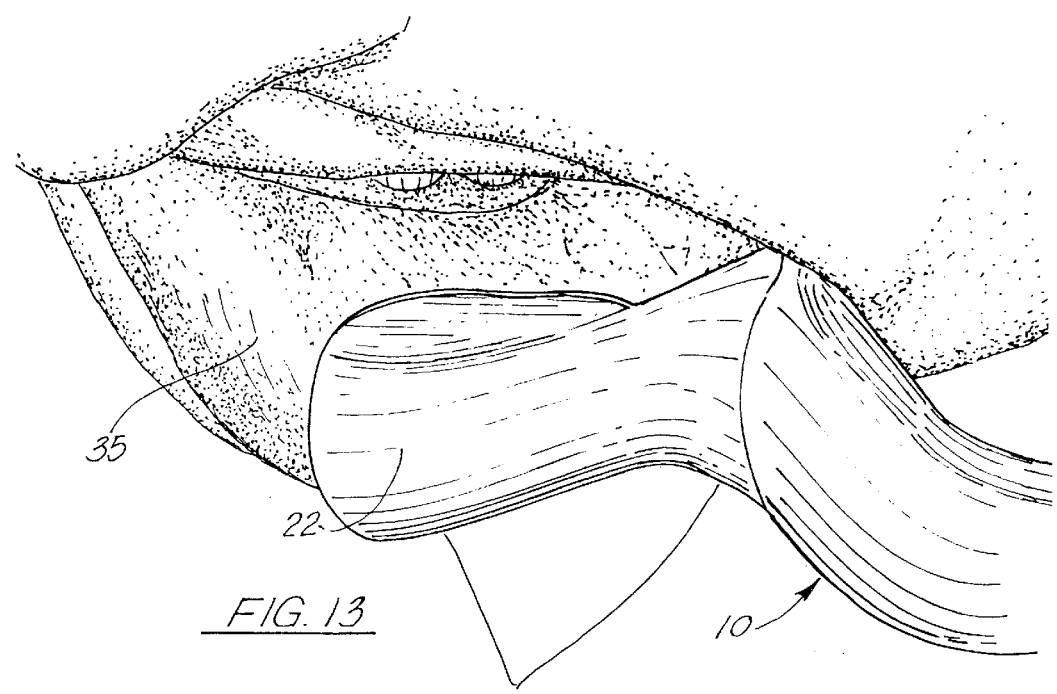
FIG. 13 illustrates an isolated view of the apparatus retracting the lower lip of a patient during use and FIG. 14 illustrates a bottom view of the apparatus being utilized to retract the cheek and lower lip of a patient as the teeth are being polished with a dental instrument.
Figure 12B:
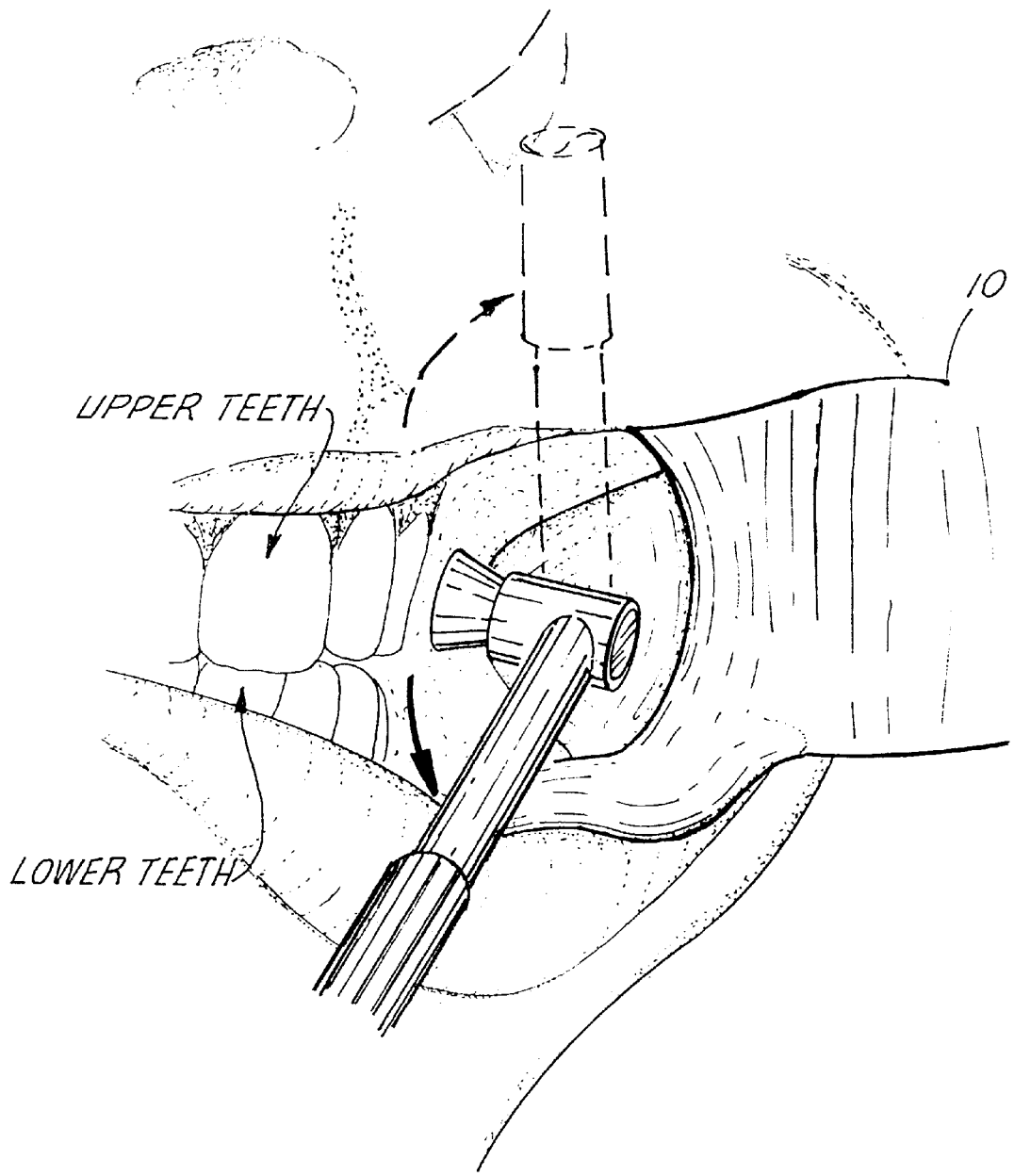

Again, as seen in FIG. 10, the apparatus 10 is seen being held again by hand 32 with the patient 30 resting her head back while the apparatus has been inserted within her mouth. The handle portion 12 is grasped by the dentist's hand 32 and the lower lip 35 is being depressed downward while the cheek retractor portion 24 is pushing the cheek 35 outward and the upper lip is being retracted upward so as to have easy access to the buccal surfaces of the patent's upper and lower posterior teeth. It should be noted that because of the position of the handle portion 12 of the apparatus and for example as seen in FIG. 3 the long axis of the handle portion 12 is approximately a 15 degree angle from the horizontal line 17. This allows a dentist to conduct work on the patient while being seated because of the angulation of the handle, so that when one pulls back it automatically retracts the cheek slightly outward and the lower lip is pushed further downward while the upper lip is retracted upward Turning now to FIGS. 11A and 11B, there is seen, again in 11A, an isolated view of the lower lip depressor portion 22 pressing downward on the lip 35 to provide a greater volume of space in vestibule 44 for conducting work. As seen in 11B, the cheek retractor portion 24 extends from the bridge portion 18, and pushes the cheek outward while the very end 25 of the cheek retractor portion 24 is curving against the rear 27 of the mouth in the vestibule 44 in order to provide an entire arcuate retraction of the cheek along its inner surface as seen in 11B. In FIGS. 12A and 12B, the apparatus 10 is again illustrated so that a lip 35 is depressed downward by depressor portion 22, the cheek of the patient is retracted outward by the cheek retractor portion 24 and the upper lip is retracted up and away from the teeth by portion 29 so that the vestibule 44 within the patient's mouth is quite enlarged and an instrument 50, such as the type of instruments that would be used to bond orthodontic appliances can be inserted easily into the vestibule 44 for making direct contact with the patient's teeth 52, particularly the rear most teeth which are normally very difficult to access during the procedure.

Again, as was discussed earlier, FIG. 13 is an isolated view of the patient's lower lip 35 being depressed downward by lip depressor portion 22 of apparatus 10 in the view.

Figure 14:
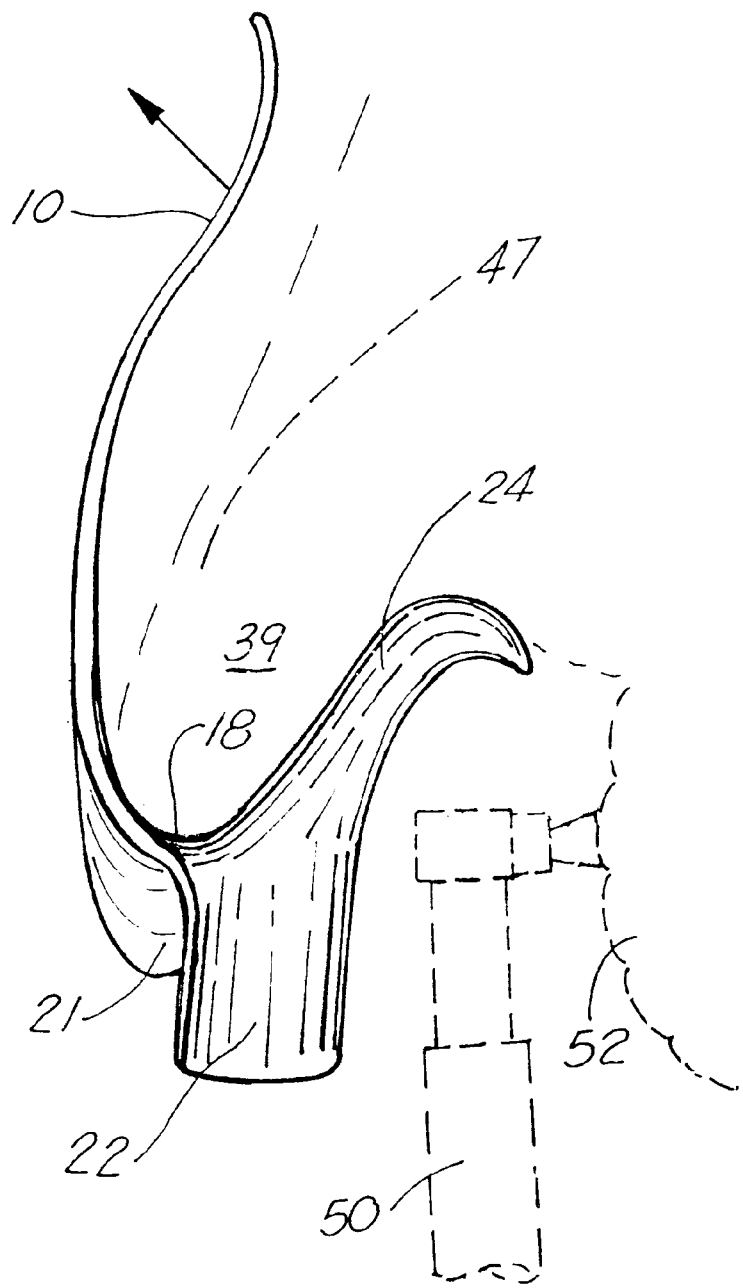

In FIG. 14, there is seen a substantially bottom view of the apparatus, again showing the linear formation of handle 10 with its slight curvature directed to bridge portion 18 wherein there is seen the lower lip depressor portion 22, the cheek retractor portion 24, and the upper lip retractor portion 29. As seen in this particular view, there is provided in phantom view the cheek 39 of the patient held within the opening 47 formed between the handle 12 and the cheek retractor portion 24 so that as the handle 12 is pulled in the direction of arrow 60, the cheek is pulled outward so that a cleaning instrument 50 of the type as was seen in FIGS. 12A and 12B may be utilized against the teeth 52 of a patient during use.

In the preferred embodiment, the apparatus of the present invention could be formed of any material such as stainless steel or molded plastic, which would be durable and light weight and would be the type of material that can be sterilized and used in the oral environment during orthodontic work. Of course, when the implement would be used on the left side, it would be a mirror image of a second implement that would have to be used on the right side by the orthodontist during orthodontic procedures or the like. The instruments would be provided in a mirror image pair. The instrument provided for use on the patient's right side would be a mirror image of that provided for use on the left.

The foregoing embodiments are presented by way of example only; the scope of the present invention is to be limited only by the following claims.

What is claimed is:

1. An improved retractor apparatus, for use during dry orthodontic dental procedures on a patient, comprising:
   a. an elongated handle portion, adapted to extend along the outer cheek toward the ear for grasping by a dentist;
   b. a lower lip depressor portion, further comprising a concave surface for engaging the lower lip;
   c. a cheek retracting portion, adapted to be positioned against an interior surface of the cheek, and terminating in a biconvex end to conform to a rear portion of the cheek the biconvex end in position behind the upper and lower second molars to retract the soft tissue away from the upper and lower second molars when positioned in the patient's mouth;
   d. an upper lip retractor portion, for engaging and retracting the upper lip;
   e. the lower lip depressor portion forcing the lower lip downward, the cheek retracting portion retracting the cheek outward and retracting soft tissue behind the upper and lower second molars down and away from the molars, and the upper lip retractor portion retracting the upper lip upward, all simultaneously, as the handle portion is pulled away from the cheek by the dentist, for defining a larger vestibule and providing other retromolar space in the patient's mouth to obtain access to the buccal surfaces of the teeth, and for establishing the dry field for conducting the dental procedure.

2. The apparatus in claim 1, wherein a long axis of the handle portion is adapted to extend at an angle approximately 30 degrees from a long axis of the cheek retractor portion.

3. The apparatus in claim 1, wherein the bridge portion is situated at the commissure of the mouth during use.

4. The apparatus in claim 2, wherein the angulated position of the handle portion provides use of the apparatus while the user is seated.

5. The apparatus in claim 1, wherein the apparatus would be formed of molded plastic or stainless steel to be sterilizable for use in a patient's mouth.

6. An improved retractor apparatus, for use during dry orthodontic dental procedures, comprising:
   a. a first elongated handle portion, adapted to extend along the outer cheek toward the ear for grasping by a dentist;
   b. a second lower lip depressor portion, further comprising a concave surface for engaging the lower lip;
   c. a third cheek retractor portion, adapted to be positioned against an interior surface of the cheek and terminating in a biconvex end to conform to a rear portion of the cheek behind the upper and lower second molars to retract the soft tissue away from the upper and lower second molars when positioned in the patient's mouth;
   d. a fourth upper lip retractor portion, for engaging and retracting the upper lip;
   e. a bridge portion interconnecting the handle portion to the lower lip depressor portion, the cheek retractor portion, and the upper lip retractor portion; and
   f. the second lower lip depressor portion forcing the lower lip downward, the cheek retracting portion retracting the cheek outward and retracting soft tissue behind the upper and lower second molars down and away from the molars, and the upper lip retractor portion retracting the upper lip upward, all simultaneously, as the handle portion is pulled away from the cheek by the dentists, for defining a larger vestibule and providing other retromolar space in the patient's mouth to obtain access to the buccal surfaces of the teeth, and for establishing the dry field for conducting the dental procedure.

7. The apparatus in claim 6, wherein a long axis of the handle portion is adapted to extend at an angle of approximately 30 degrees upward from the horizontal, using a long axis of the cheek retractor portion as the horizontal.

8. The apparatus in claim 6, wherein the angulation of the handle portion provides for use of the apparatus while the user is seated.

9. The apparatus in claim 6, wherein the apparatus would be formed of molded plastic or stainless steel to be sterilizable for use in the mouth.

10. An improved retractor apparatus, for use during dry orthodontic dental procedures, comprising:
   a. a first elongated handle portion, is adapted to extend along the outer cheek toward the ear for grasping by a dentist;

b. a second lower lip depressor portion, further comprising a concave surface for engaging the lower lip;

c. a third cheek retractor portion, adapted to be positioned against an interior surface of the cheek, and terminating in a biconvex end to conform to a rear portion of the cheek behind the upper and lower second molars to retract the soft tissue away from the upper and lower second molars when positioned in the patient's mouth;

d. a fourth upper lip retractor portion, for engaging and retracting the upper lip;

e. a bridge portion interconnecting the handle portion to the lower lip depressor portion, the cheek retractor portion, and the upper lip retractor portion and situated at the commissure of the mouth during use; and f. the second lower lip depressor portion forcing the lower lip downward, the cheek retracting portion retracting the cheek outward and retracting soft tissue behind the upper and lower second molars down and away from the molars, and the upper lid retractor portion retracting the upper lip upward, all simultaneously, as the handle portion is pulled away from the cheek by the dentist, for defining a larger vestibule and providing other retromolar space in the patient's mouth to obtain access to the buccal surfaces of the teeth, and for establishing the dry field for conducting the dental procedure.

11. The apparatus in claim 10, wherein the long axis of the handle portion is adapted to extend at an angle of approximately 30 degrees from the long axis of the cheek retractor portion.

12. The apparatus in claim 10, wherein the angulated position of the handle portion provides for use of the apparatus while the user is seated and the patient is essentially supine in a dental chair.

13. The apparatus in claim 10, wherein the apparatus would be formed of molded plastic or stainless steel so as to be sterilizable for use in the mouth.

14. The apparatus in claim 10, wherein the handle portion further comprises a thin waist portion terminating in a broader end portion of the handle, for allowing use of the apparatus yet preventing the hand grasping the handle from slipping off of the handle during use.

* * * * *